United States Patent
Bach

(10) Patent No.: US 9,664,575 B2
(45) Date of Patent: May 30, 2017

(54) SELF-CALIBRATING RESISTIVE FLEXURE SENSOR

(71) Applicant: General Electric Company, Schenectady, NY (US)

(72) Inventor: James Carter Bach, Seymour, IN (US)

(73) Assignee: Haier US Appliances Solutions, Inc., Wilmington, DE (US)

( * ) Notice: Subject to any disclaimer, the term of this patent is extended or adjusted under 35 U.S.C. 154(b) by 36 days.

(21) Appl. No.: 14/487,127

(22) Filed: Sep. 16, 2014

(65) Prior Publication Data

US 2015/0000418 A1     Jan. 1, 2015

Related U.S. Application Data

(62) Division of application No. 13/670,982, filed on Nov. 7, 2012, now Pat. No. 8,863,586.

(51) Int. Cl.
| | |
|---|---|
| *G01L 1/04* | (2006.01) |
| *G01N 3/20* | (2006.01) |
| *H01C 17/06* | (2006.01) |
| *H01C 10/10* | (2006.01) |
| *H01C 10/16* | (2006.01) |

(Continued)

(52) U.S. Cl.
CPC ............ *G01L 1/04* (2013.01); *G01D 18/00* (2013.01); *G01F 1/56* (2013.01); *G01K 7/16* (2013.01); *G01L 1/2262* (2013.01); *G01N 3/20* (2013.01); *G01N 27/04* (2013.01); *H01C 10/10* (2013.01); *H01C 10/16* (2013.01); *H01C 17/06* (2013.01);

(Continued)

(58) Field of Classification Search
CPC .... G01D 18/00; G01D 18/002; G01D 18/004; G01D 18/006; G01F 1/56; G01F 1/586; G01K 7/16; G01K 7/18; G01K 7/183; G01L 1/04; G01L 1/044; G01L 1/2262; G01N 27/04; G01N 3/20; H01C 17/06; H01C 17/00; H01C 17/006; H01C 17/065; H01C 10/10; H01C 10/106; H01C 10/16; H01C 10/18; H01C 10/22; Y10T 29/49082; Y10T 29/49087; Y10T 29/49099; Y10T 29/49103
USPC ..................... 73/774; 29/620, 621
See application file for complete search history.

(56) References Cited

U.S. PATENT DOCUMENTS

| | | |
|---|---|---|
| 3,614,678 A | 10/1971 | Engeler et al. |
| 5,157,372 A | 10/1992 | Langford |

(Continued)

*Primary Examiner* — Michael A Lyons
*Assistant Examiner* — Philip Cotey
(74) *Attorney, Agent, or Firm* — Dority & Manning, P.A.

(57) ABSTRACT

A variable resistance flexure sensor, and a system and method of controlling an appliance using a variable resistance flexure sensor are provided. The sensor can include a substrate having a flexible portion and a non-flexible portion. A plurality of electrically resistive elements, such as a first resistive element and a second resistive element, can be disposed on the substrate where at least one resistive element is exclusively within the non-flexible portion of the substrate and at least one resistive element is within the flexible portion of the substrate. The resistive element within the non-flexible portion of the substrate can act as a reference resistance for the flexure sensor and can be used as, or as part of, a biasing network for the electrically resistive element within the flexible portion of the substrate. The flexure sensor can be used within an appliance to detect various conditions such as temperature, moisture, etc.

19 Claims, 8 Drawing Sheets

(51) Int. Cl.
*G01L 1/22* (2006.01)
*G01D 18/00* (2006.01)
*G01F 1/56* (2006.01)
*G01K 7/16* (2006.01)
*G01N 27/04* (2006.01)

(52) U.S. Cl.
CPC .... *Y10T 29/49099* (2015.01); *Y10T 29/49103* (2015.01)

(56) References Cited

U.S. PATENT DOCUMENTS

| | | | |
|---|---|---|---|
| 5,583,476 A | 12/1996 | Langford | |
| 6,034,404 A | 3/2000 | Soares | |
| 7,573,365 B2 | 8/2009 | Beck et al. | |
| 8,047,083 B2 | 11/2011 | Puzio et al. | |
| 2001/0001236 A1 | 5/2001 | Lake | |
| 2003/0029245 A1* | 2/2003 | Izadnegahdar | G01L 9/0055 73/753 |
| 2003/0079551 A1* | 5/2003 | Hata | G01L 1/2287 73/760 |
| 2005/0050959 A1* | 3/2005 | Ooba | G01L 1/2287 73/775 |
| 2006/0238291 A1* | 10/2006 | Beck | H01C 10/16 338/200 |
| 2007/0279182 A1* | 12/2007 | Kodas | H01C 17/065 338/22 R |
| 2009/0031818 A1* | 2/2009 | McKinnell | H04R 17/02 73/727 |
| 2009/0056353 A1 | 3/2009 | Sunderland | |
| 2010/0018634 A1 | 1/2010 | Takahashi et al. | |
| 2010/0171583 A1* | 7/2010 | Iovine | H01C 10/106 338/211 |
| 2012/0090387 A1 | 4/2012 | Djakov | |
| 2013/0033323 A1* | 2/2013 | Scuderi | G01D 1/16 330/257 |

\* cited by examiner

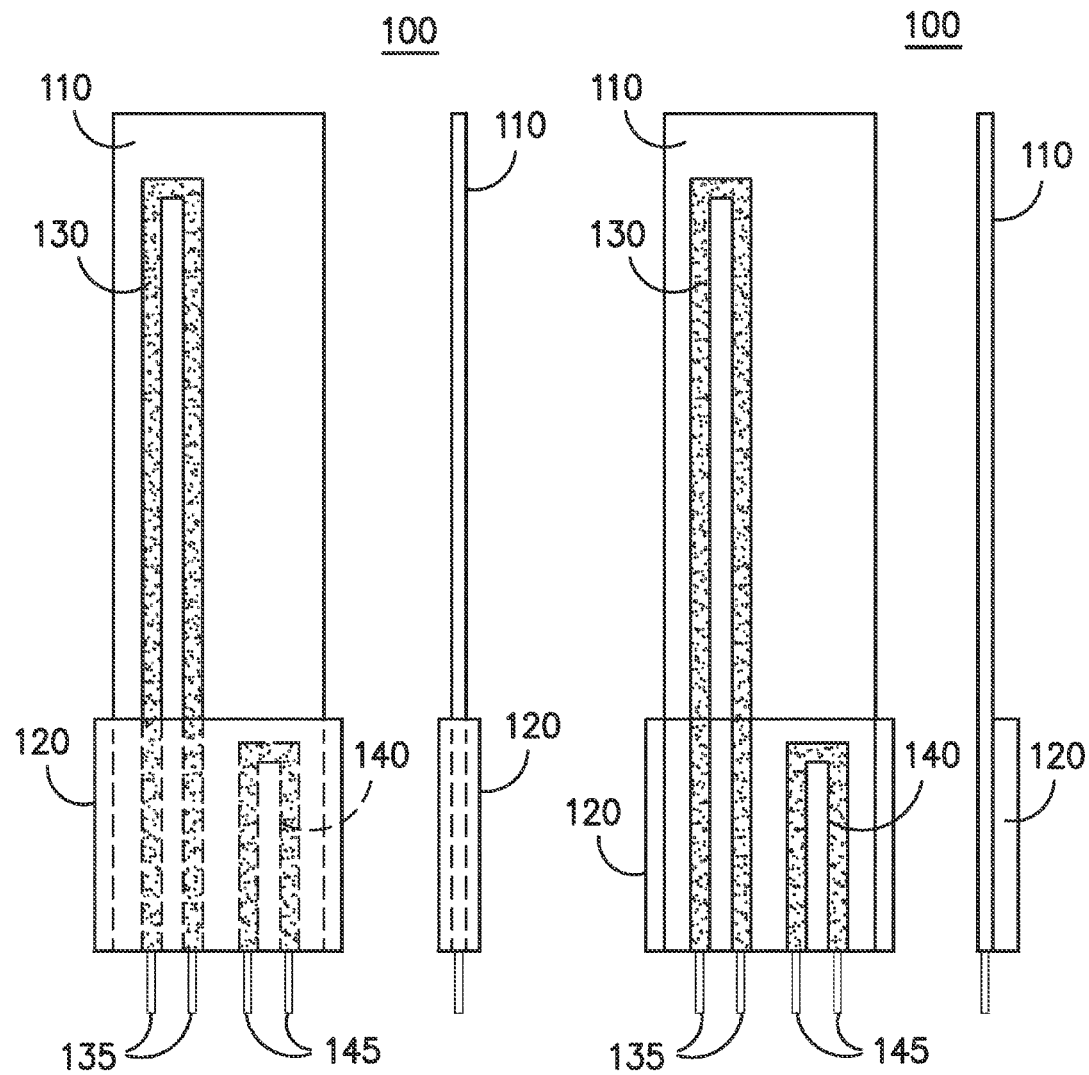

SELF-CALIBRATING RESISTIVE FLEXURE SENSOR

FIELD OF THE INVENTION

The present subject matter relates generally to a self-calibrating resistive flexure sensor, and more particularly to, a method and system to improve appliance control using the self-calibrating resistive flexure sensor.

BACKGROUND OF THE INVENTION

Flexible resistive sensors, such as flexure sensors, flex sensors, bending sensors, strain gages, etc., can be used to measure various conditions such as temperature, moisture, air flow, mechanical stress, etc. A variable resistance element can be provided on a flexible substrate that changes shape and/or dimensions based on the condition being measured. More specifically, an electrical resistance of the resistive element is variable corresponding to a change in flexure of the flexible substrate. The flexure of the substrate, and thus the resistive element, is caused by the physical quantity to be measured with the sensor. For example, a flexure sensor can be placed in an air pathway (duct, pipe, tube) and used to measure the air flow rate (velocity) within the pathway.

Conventionally, the electrically resistive elements of flexure sensors are manufactured using a printing technique such as screen printing or by a metal deposition technique such as sputtering. However, the electrically resistive elements formed using these techniques can have inconsistent properties due to a variety of factors such as stencil accuracy, material thickness, and material composition. These factors can vary from day to day during the manufacturing process. Therefore, the response (transfer function) of any device that utilizes a flexure sensor having resistive elements created using these techniques are not typically uniform (consistent) for all sensors but rather unique for each device. In other words, a device using a resistive flexure sensor needs a way to be "calibrated" as a system to compensate for the generally loose tolerances of the sensor.

In a conventional approach, the resistive element of a flexure sensor is coupled to a biasing/scaling network configured to provide a predetermined amount of current through the resistive sensor element so as to produce a flexure-dependent variable voltage within some desired range. One or more fixed-value resistors are generally used to bias the resistive element of the flexure sensor, including a common resistor divider or Wheatstone Bridge configuration. However, changes in ambient temperature in the system can non-uniformly affect the resistance response of the resistive element of the flexure sensor and the biasing network because the temperature coefficients of the resistive flexure sensing element and the biasing network are not exactly the same. Therefore, calibration of the sensor is difficult because the biasing network cannot adequately compensate for the non-uniform variable response of the resistive element of the sensor.

Thus, a need exists for a flexure sensor having an improved biasing network for self-calibrating the flexure sensor and cancelling-out the effects of part-to-part variation and temperature-dependent shifts.

BRIEF DESCRIPTION OF THE INVENTION

Aspects and advantages of the invention will be set forth in part in the following description, or may be apparent from the description, or may be learned through practice of the invention.

One exemplary aspect of the present disclosure is directed to a flexure sensing device. The flexure sensing device includes a substrate having a flexible portion and a non-flexible portion. The flexure sensing device further includes a first resistive element formed on or within the flexible portion of the substrate. The first resistive element has a variable electrical resistance dependent on a change in flexure of the flexible portion of the substrate. The flexure sensing device further includes a second resistive element formed on or within the non-flexible portion of the substrate. The second resistive element provides a reference resistance for the flexure sensing device.

Another exemplary aspect of the present disclosure is directed to a method of manufacturing a flexure sensing device. The method includes depositing first and second resistive elements on or within a flexible substrate. The first resistive element has a variable electrical resistance dependent on a change in flexure of the flexible substrate. The method further includes forming a non-flexible portion of the substrate such that the second resistive element is disposed on or within the non-flexible portion of the substrate. The second resistive element provides a reference resistance for the flexure sensing device.

Yet another exemplary aspect of the present disclosure is directed to a method for operating an appliance. The method can include monitoring a state of the appliance using a flexure sensing device. The flexure sensing device has a flexible portion and a non-flexible portion. A first resistive element can be formed on or within the flexible portion. The first resistive element can have a variable resistance dependent on a change in flexure of the flexible portion. The flexure sensing device can further include a second resistive element formed on or within the non-flexible portion of the substrate. The second resistive element can provide a reference resistance for the flexure sensing device. The method can further include detecting an output of the first resistive element and an output of the second resistive element of the flexure sensing device; determining a change in flexure of the substrate of the flexure sensing device based on the output of the first resistive element and the output of the second resistive element; and controlling the appliance based on the determined change in flexure of the substrate of the flexure sensing device.

These and other features, aspects and advantages of the present invention will become better understood with reference to the following description and appended claims. The accompanying drawings, which are incorporated in and constitute a part of this specification, illustrate embodiments of the invention and, together with the description, serve to explain the principles of the invention.

BRIEF DESCRIPTION OF THE DRAWINGS

A full and enabling disclosure of the present invention, including the best mode thereof, directed to one of ordinary skill in the art, is set forth in the specification, which makes reference to the appended figures, in which:

FIG. 1 depicts a perspective and longitudinal side view of an exemplary flexure sensor according to an exemplary embodiment of the present disclosure;

FIG. 2 depicts a perspective view and a longitudinal side view of an exemplary flexure sensor according to an exemplary embodiment of the present disclosure;

DETAILED DESCRIPTION OF THE INVENTION

Figure 3:
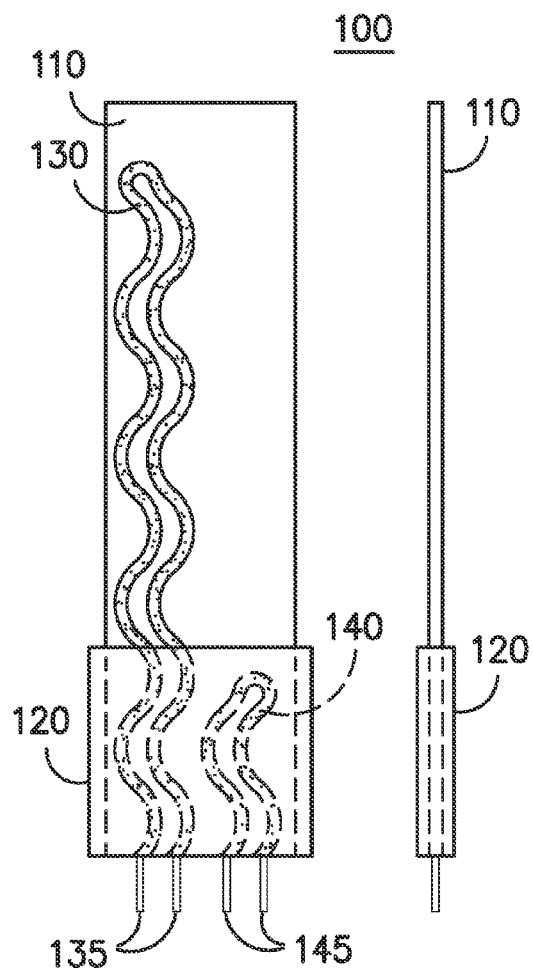
FIG. 3 depicts a perspective view and a longitudinal side view of an exemplary flexure sensor according to an exemplary embodiment of the present disclosure.

Reference now will be made in detail to embodiments of the invention, one or more examples of which are illustrated in the drawings. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment can be used with another embodiment to yield a still further embodiment. Thus, it is intended that the present invention covers such modifications and variations as come within the scope of the appended claims and their equivalents.

Generally, the present disclosure is directed to a flexure sensor, and a system and method of controlling an appliance using a flexure sensor. The sensor can include a substrate having a flexible portion and a non-flexible portion. A plurality of resistive elements, such as a first resistive element and a second resistive element, can be disposed on or within the substrate. The first resistive element can have a variable resistance dependent on the flexure of the flexible portion. The second resistive element can be disposed exclusively within the non-flexible portion of the substrate. The second resistive element can provide a reference resistance that can be used as part of a biasing network for the flexure sensor.

In particular, the first resistive element can be formed on or within the flexible portion of the substrate such that the first resistive element is allowed to flex while the second element is constrained on or within the non-flexible portion of the substrate. This allows the second resistive element to provide the reference resistance for biasing (e.g. as part of a bias network) the flexure sensor device. The reference resistance, formed by the second resistive element within the non-flexible portion of the flexure sensor, may be used as the "fixed" or "known" element of bias network, such as a simple two resistor divider network or within a Wheatstone Bridge network. Because this second resistance can be created using identical techniques and materials as the first resistance within the flexible portion of the flexure sensor, its nominal resistance tracks (matches) closely with the unflexed (relaxed, natural) state of the first resistance, and the temperature coefficient of resistance (aka TCR) of the two resistive elements also tracks (matches) closely. Thus, it can be seen that the two most problematic aspects of resistive flexure sensors are, for the most part, cancelled-out.

The sensor can be used within an appliance to detect various conditions such as temperature, moisture, air flow, etc. A change in condition can be determined based on outputs of the resistive elements of the sensor. As the substrate flexes in response to changing conditions, the outputs of the first resistive element can be monitored for the change in resistance. The output of the second resistive element can be used to bias the output of the first resistive element such that the flexure sensor is self-calibrating.

The flexure sensor according to aspects of the present disclosure can provide various advantages. For instance, any inconsistencies in manufacturing resulting from the depositing of the first and second resistive elements will be uniform across the resistive elements because the resistive elements can be formed on the substrate at the same time. In addition, any deterioration of tolerance and/or stability of the resistive elements over time would also be uniform because all the resistive elements are exposed to the same environmental conditions throughout the lifetime of the sensor. In addition, when the sensor is coupled within a circuit for control, no additional circuitry elements are needed to bias the sensor.

FIGS. 1-4 illustrate exemplary resistive flexure sensors 100 according to exemplary embodiments of the present disclosure. For instance, as shown in FIG. 1, the sensor 100 can include a substrate having a flexible portion 110 and a non-flexible portion 120. A first resistive element 130 can be disposed on or within the flexible portion 110 and a second resistive element 140 can be disposed on or within the non-flexible portion 120.

The flexible portion 110 of the substrate can include any electrically insulating material that is suitable as a substrate and is configured to retain form and shape while also being elastically flexible or bendable. For instance, the flexible material can be a plastic, resin, polymer, silicone, etc. (e.g. Kapton or polyimide film). The flexible material can also be a thin sheet of an electrically-conductive material (e.g. aluminum, steel, copper, etc.) which is then coated with a non-conductive layer (e.g. plastic, paint, etc.) prior to application of the resistive element material. Preferably, the flexible portion 110 of the substrate can flex without causing an electrical discontinuity or open circuit in the first and/or second resistive elements 130, 140.

The non-flexible portion 120 can be formed from a substantially rigid material that prevents flexing. For instance, the non-flexible portion 120 can be a rigid material such as plastic, epoxy, bakelite, etc. The non-flexible portion 120 can be formed separately from the substrate and then applied to the flexible portion 110 of the substrate. For instance, the non-flexible portion 120 can be injection molded and then coupled to the flexible portion of the substrate, or even injection molded around the flexible portion of the substrate (e.g. over-molded). Alternatively, the non-flexible portion 120 of the substrate can be formed by modifying a portion of the flexible substrate 110.

When the non-flexible portion 120 of the substrate is formed separately, it can be coupled to the flexible portion 110 such that it surrounds a portion of the flexible portion 120 of the substrate as illustrated in FIG. 1. Alternatively, the non-flexible portion 120 can be coupled to a top surface of the substrate and/or a bottom surface of the substrate. For instance, as illustrated in FIG. 2, the non-flexible portion 120 can be coupled to a surface opposite to the surface where the resistive elements 130 and 140 are deposited.

A plurality of electrically resistive elements 130 and 140 can be disposed on a surface of the substrate, such as a top or bottom surface of the substrate. The electrically resistive elements can be formed of a material that has electrical properties, including resistive properties. For instance, the electrically resistive elements 130 and 140 can be a conductive material, such as a conductive ink, deposited on the substrate using a silk-screen printing process such that the resistive elements 130 and 140 are formed essentially simultaneously.

Figure 4:
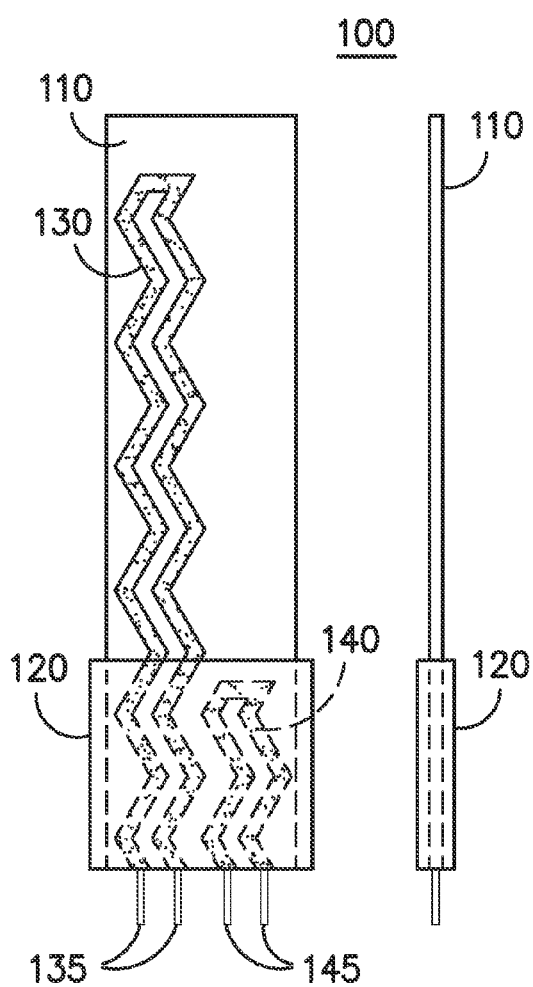
FIG. 4 depicts a perspective view and a longitudinal side view of an exemplary flexure sensor according to an exemplary embodiment of the present disclosure.

As shown in FIG. 1, the electrically resistive elements 130 and 140 can have rectangular "U" shape. Alternatively, as shown in as shown in FIGS. 3 and 4, the electrically resistive elements 130 and 140 can have non-linear symmetrical shapes. The electrically resistive elements 130 and 140 can have any shape, arrangement, and/or configuration. For instance, the electrically resistive elements 130 and 140 can have the same shape or different shapes. The electrically resistive elements 130 and 140 can also be continuous or segmented elements.

Referring back to FIG. 1, the first resistive element 130 having connectors 135 can be formed in both the flexible portion 110 and the non-flexible portion 120 of the substrate. A second resistive element 140 having connectors 145 can be formed exclusively within the non-flexible portion 120. The sensor 100 can be mounted directly to a printed circuit board (PCB) such that connectors 135 and 145 can be electrically coupled to contacts in the PCB. This coupling of the resistive elements to the PCB can be accomplished by means of soldering the connectors 135 and 145 into holes in the PCB, or by means of inserting connectors 135 and 145 into a connector that has been soldered onto the PCB.

When conditions change causing the flexible portion 110 of the substrate to flex, the resistance of the first resistive element 130 changes and an output indicative of the change in flexure (i.e. a change in voltage/current resulting from the change in resistance) is supplied to the connectors 135. Since the second resistive element 140 is exclusively within the non-flexible portion 120 of the substrate, as the substrate flexes there should be substantially no change in the resistance of the second resistive element 140. For the purposes of this application, "substantially no change" can include up to a 10% change in the output indicative of the resistance of the second resistive element 140. As a result, the second resistive element 140 can be used as a reference resistance for the flexure sensor.

The second resistive element 140 can be formed from the same material as the first resistive element 130 and can be formed on the same substrate as the first resistive element 130 using similar processing conditions. For example, the first resistive element 130 and the second resistive element 140 can be deposited on the substrate using a silk-screen printing process such that the resistive elements 130 and 140 can be formed essentially simultaneously; a metal sputtering technique can also be used to simultaneously create the resistive elements. In this manner, the second resistive element 140 can provide improved biasing of the flexure sensor because it is subject to the same operating characteristics and conditions as the first resistive element 130.

Figure 5:
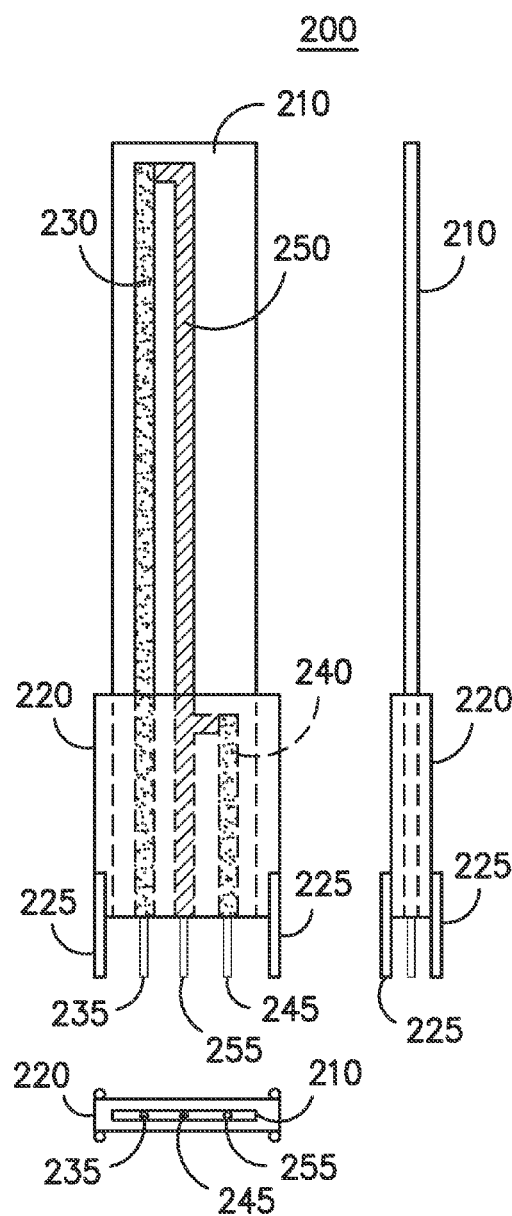
FIG. 5 depicts a perspective view, a longitudinal side view, and a horizontal side view of an exemplary flexure sensor according to an exemplary embodiment of the present disclosure.
Figure 6:
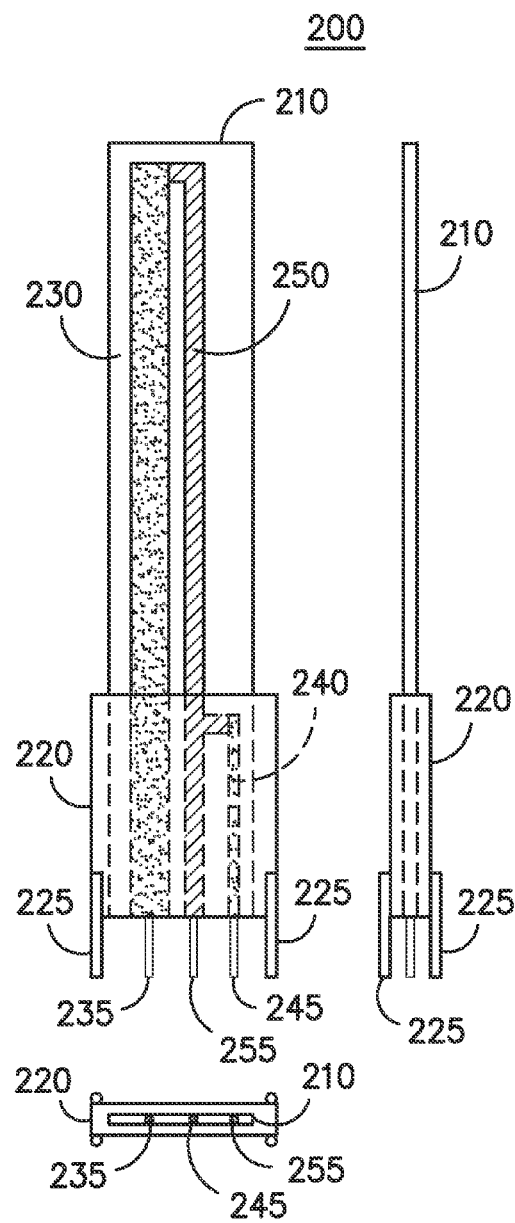
FIG. 6 depicts a perspective view, a longitudinal side view, and a horizontal side view of an exemplary flexure sensor according to an exemplary embodiment of the present disclosure.

FIGS. 5 and 6 illustrate an exemplary flexure sensor 200 according to alternative exemplary embodiments of the present disclosure. Sensor 200 can include a substrate having a flexible portion 210 and a non-flexible portion 220. A first resistive element 230 providing an output through terminal 235 can be disposed on or within the flexible portion 210. A second resistive element 240, providing an output through terminal 245 can be disposed on or within the non-flexible portion 220.

A common conductive element 250 can be coupled between the first resistive element 230 and the second resistive element 240 such that the common conductive element is deposited in both the flexible portion 210 and the non-flexible portion 220 of the substrate. The common conductive element 250 can be coupled to terminal 255. The common conductive element 250 can have any shape, size, and/or configuration. In one implementation, the common conductive element 250 can be constructed of a material whose resistance remains essentially unchanged with flexure of the flexible portion of the substrate. Ideally the common conductive element 250 is constructed of a material which offers very low electrical resistance, relative to the two flexure-sensitive resistive elements.

As previously discussed, the resistive elements 230 and 240 can have any shape, size, and/or configuration. For instance, as shown in FIGS. 5 and 6, the widths of the first resistive element 230 and the second resistive element 240 can also be variable. More particularly, in FIG. 5, the widths of the first resistive element 230 and the second resistive element 240 are essentially the same. As a result, the relative resistances of the first resistive element 230 and the second resistive element 240 are different based on the ratio of their lengths. In FIG. 6, the width of the longer first resistive element 230 is greater (wider) than the width of the shorter second resistive element 240. As a result, the resistances of the first resistive element 230 and the second resistive element 240 can be made nearly identical. Any resistance ratio (in the non-flexed condition) can be achieved using these geometric scaling techniques.

The sensor 200 can be mounted in a PCB using mounting pins 225 where the mounting pins 225 can be non-conductive. In addition, outputs 235, 245 of the resistive elements 230 and 240, and the output 255 of the common conductive element 250 can be electrically coupled to contacts in the PCB.

Figure 7:
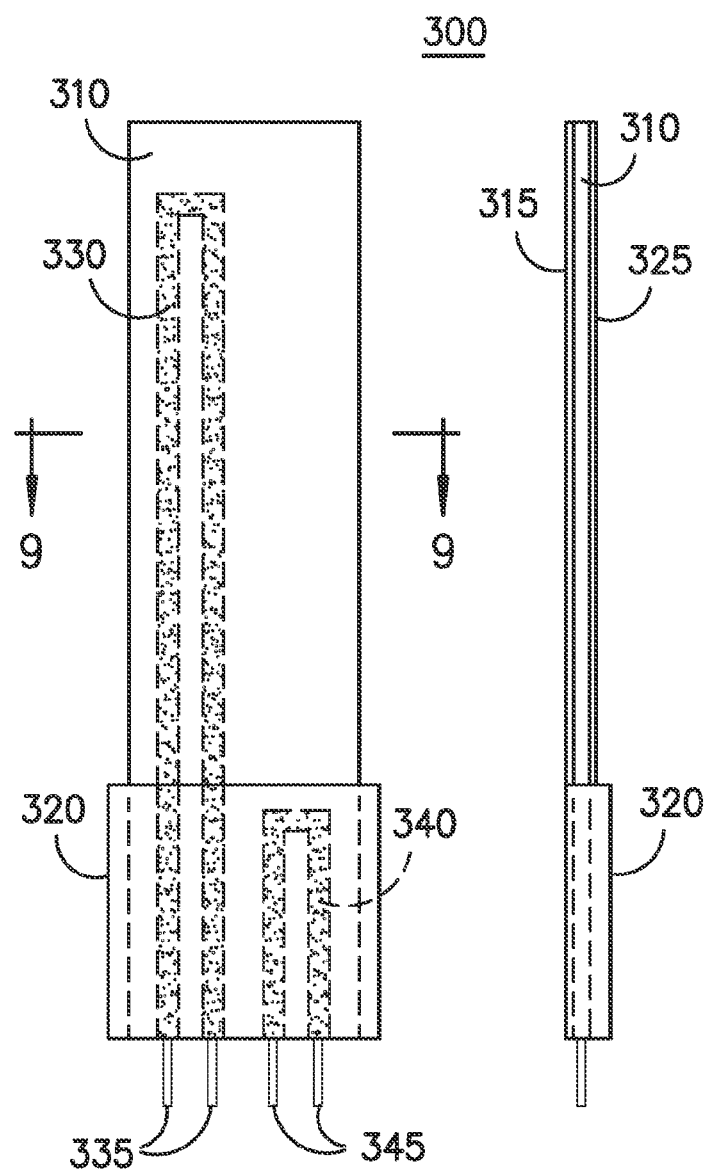
FIG. 7 depicts a perspective view and a longitudinal side view of an exemplary flexure sensor according to an exemplary embodiment of the present disclosure.
Figure 8:
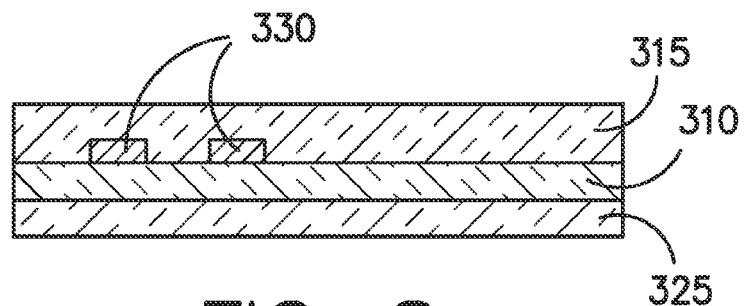
FIG. 8 depicts a cross-sectional view of the exemplary flexure sensor of FIG. 7 according to an exemplary embodiment of the present disclosure.

FIGS. 7 and 8 illustrate an exemplary flexure sensor 300 according to another exemplary embodiment of the present disclosure. Specifically, FIG. 7 depicts a perspective view of the sensor 300 and FIG. 8 depicts a cross-sectional view of the sensor 300. The flexure sensor 300 can include a substrate having a flexible portion 310 and a non-flexible portion 320. A first resistive element 330 providing an output through terminals 335 can be disposed on or within the flexible portion 310. A second resistive element 340 providing an output through terminals 345 can be disposed on or within the non-flexible portion 310.

As illustrated in FIG. 8, the first resistive element 330 and flexible portion 310 can provided between encapsulation layers 315 and 325. The encapsulation layers 315 and 325 can be made of any material that would protect the sensor 300 from degradation and/or malfunction. For instance, the encapsulation layers 315 and 325 can prevent the resistive elements 330 and 340 from premature erosion. In addition, the encapsulation layers 315 and 325 can prevent unwanted moisture from permeating the sensor.

Figure 9:
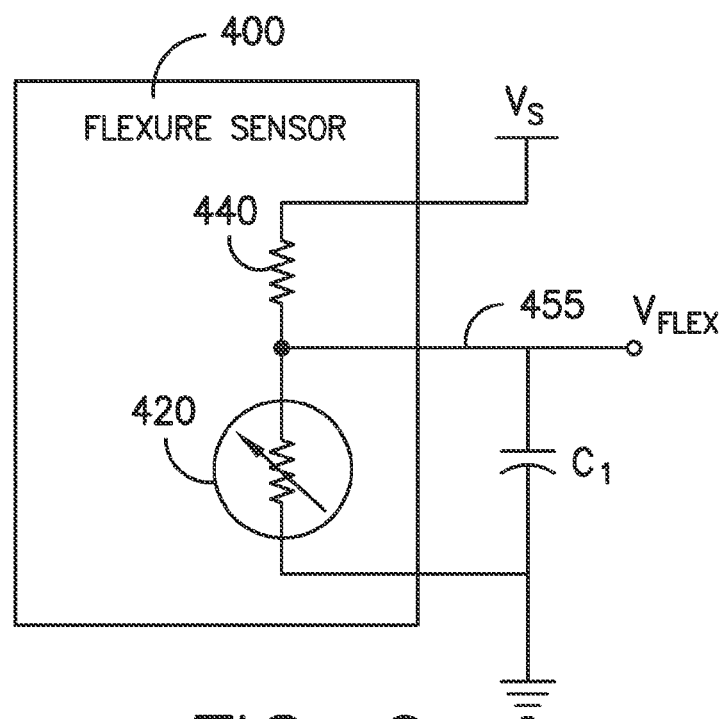
FIGS. 9-11 depict exemplary biasing networks used in conjunction with flexure sensors according to exemplary embodiments of the present disclosure.
Figure 10:
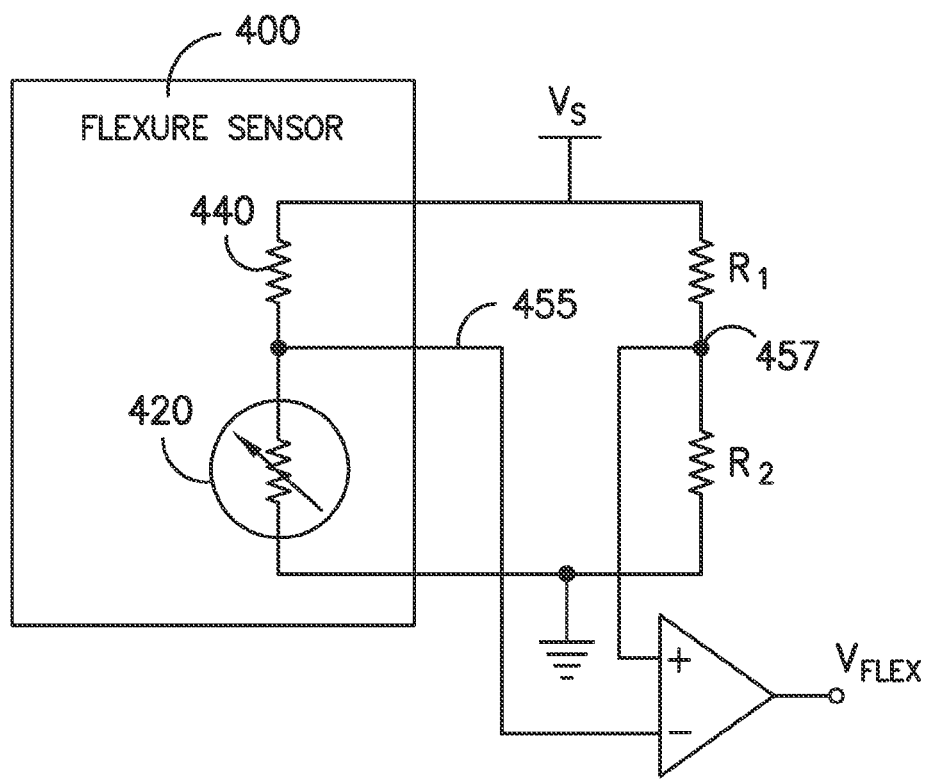
Figure 11:
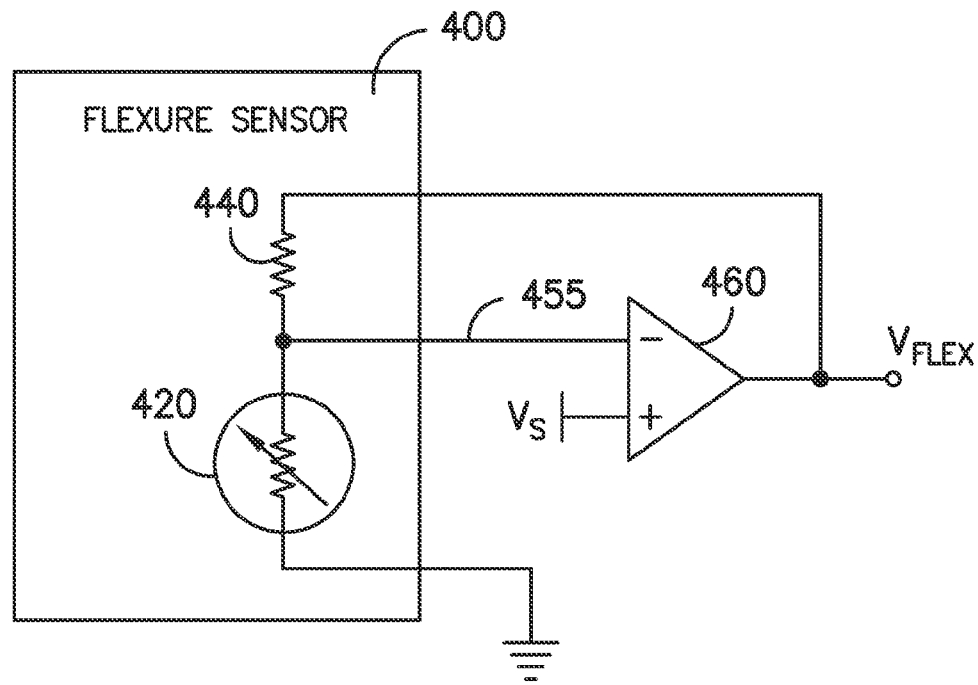

FIGS. 9-11 illustrate the use of an exemplary flexure sensor 400 in conjunction with various bias networks according to exemplary embodiments of the present disclosure. In particular, FIG. 9 depicts the exemplary flexure sensor 400 used as part of a simple two resistor divider network. More particularly, the flexure sensor 400 includes a first resistive element 420 located on or within a flexible portion of the substrate a second resistive element 440 located on or within a non-flexible portion of the substrate. The first resistive element 420 and the second resistive element 440 can form a simple two resistor divider network. The second resistive element 440 acts as the reference resistance for the flexure sensor 400. A common terminal 455 coupled between the first resistive element 420 and the second resistive element 440 can provide an output $V_{flex}$ signal (across e.g. capacitor C1) as the output of the flexure sensor 400.

FIG. 10 depicts the exemplary flexure sensor 400 used as part of a Wheatstone Bridge configuration. In particular, the first resistive element 420 and the second resistive element 440 are used in conjunction with resistors R1 and R2 to provide a Wheatstone Bridge. The second resistive element 440 acts a reference resistance for the flexure sensor device. In this arrangement, the common terminal 455 and a node 457 between resistors R1 and R2 are coupled as inputs to a suitable amplifier circuit 460. The output of the amplifier circuit 460 provides output $V_{flex}$ as the output of the flexure sensor 400.

FIG. 11 depicts the exemplary flexure sensor 400 used as part of a resistance to voltage converter bias network. Similar to FIGS. 9 and 10, the flexure sensor 400 includes a first resistive element 420 located on or within a flexible portion of the substrate a second resistive element 440 located on or within a non-flexible portion of the substrate. The second resistive element 440 acts as a reference resistance for the flexure sensor 400. In the arrangement of FIG. 11, the common terminal 455 of the flexure sensor 400 as well a constant voltage $V_s$ are provided to an amplifier circuit 460. The output of the amplifier circuit 460 provides output $V_{flex}$ as the output of the flexure sensor 400. The output $V_{flex}$ is also used as a feedback coupled to the second resistive element 440.

FIGS. 9-11 illustrate exemplary bias network configurations for purposes of illustration and discussion. Those of ordinary skill in the art, using the disclosures provided herein, should understand that any suitable bias network configuration can be used without deviation from the scope of the present disclosure.

Figure 12:
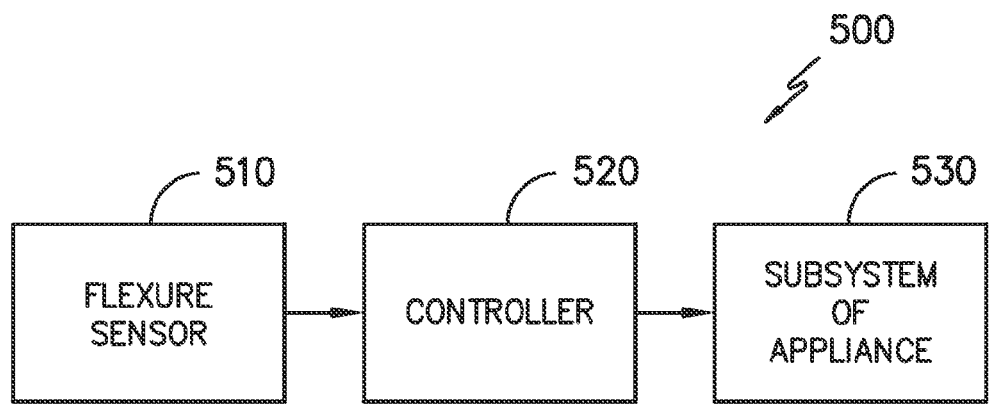
FIG. 12 depicts a block diagram of an appliance control system according to an exemplary embodiment of the present disclosure.
Figure 13:
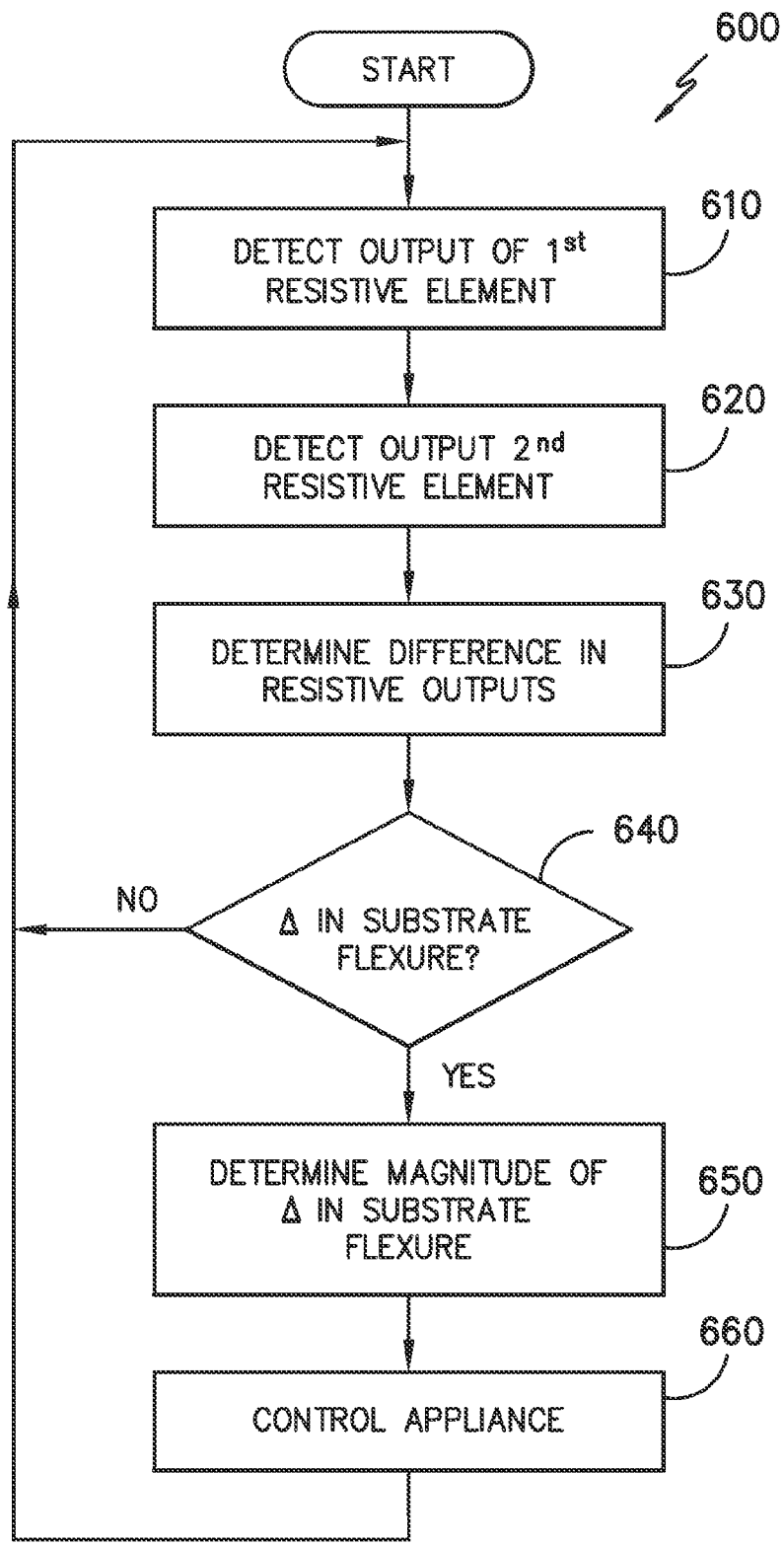
FIG. 13 depicts a flow diagram of an exemplary method of controlling an appliance according to an exemplary embodiment of the present disclosure.

FIG. 12 illustrates a block diagram of an appliance control system 500 according to an exemplary embodiment of the present disclosure. System 500 can include a flexure sensing device 510, a controller 520, and a subsystem of the appliance 530.

System 500 can be used in any appliance in which a condition can be monitored using flexure sensing device 510 such as a refrigerator, an oven, an HVAC unit, an air conditioner, a clothes dryer, an air conditioner, a space heater, a dehumidifier, a humidifier, a range hood, a bathroom fan, a furnace, etc. For instance, the flexure sensing device 410 can be disposed to detect air flow in the cooling pathway of an oven, with the controller configured to disable the heating elements of the oven if the detected air flow is insufficient. Alternatively, the flexure sensing device 510 can be disposed in a compressor of a refrigerator to detect, with the controller configured to disable the compressor if the detected moisture level is too great.

Controller 520 can monitor the output of the flexure sensing device 410 and control the appliance accordingly. For instance, the controller 420 can monitor the output of a first electrically resistive element of the flexure sensing device 410 and the output of a second electrically resistive element of the same flexure sensing device to determine a calibrated output of the sensing device 410 based on a difference between the output of the first electrically resistive element and the second electrically resistive element.

The controller 520 can be positioned in any location in the appliance. In addition, when controller 520 is a single controller it can be the only controller in the appliance such that controller 520 controls all operations of the appliance. Alternatively, when the appliance includes a plurality of controllers, controller 420 can be a sub-controller coupled to the overall appliance controller or it could be the overall appliance controller. If controller 520 is a sub-controller, it can be located with the overall appliance controller or be separate from the overall appliance controller.

By way of example, any/all of the "controllers" discussed in this disclosure, may include a memory and one or more processing devices such as microprocessors, CPUs or the like, such as general or special purpose microprocessors operable to execute programming instructions or micro-control code associated with operation of an appliance. The memory may represent random access memory such as DRAM, or read only memory such as ROM or FLASH. In one embodiment, the processor executes programming instructions stored in memory. The memory may be a separate component from the processor or may be included onboard within the processor. Alternatively, the controller might also be constructed without using a microprocessor, using a combination of discrete analog and/or digital logic circuitry (such as amplifiers, integrators, comparators, flip-flops, AND gates, and the like) to perform the oven control functionality instead of relying upon software.

In a particular embodiment of the present disclosure, the flexure sensing device 510 can be implemented to monitor a condition present in an appliance. Controller 520 can monitor the output of the flexure sensing device 510. When a change in the condition causes the flexure sensing device to flex, the controller 520 can detect the resistance of a first resistance element and the second resistance element. The controller 520 can determine a difference between the resistance detected at the first resistance element and the second resistance element to determine a change in the flexure of the substrate. The difference can be compared to a predetermined threshold where the predetermined threshold can be a predetermined range or value. When the difference exceeds or falls below the predetermined threshold, the controller 520 can control a subsystem of the appliance 530.

Alternatively, the difference between the detected resistance of the first resistance element and the second resistance element can be compared to a look-up table, algorithm, equation, or model to determine a magnitude of the change in flexure of the substrate. The controller 520 can variably control the subsystem of the appliance based on the magnitude of the change in flexure of the substrate.

For example, when the appliance is an oven and the flexure sensing device 510 is disposed within an air duct of the oven to monitor the air flow, the system 500 can perform as follows. The flexure sensing device 510 can be mounted to a PCB in the air duct and be configured to monitor the air flow in the air duct. As the air flow causes the sensing device 510 to flex, the resistance of the first resistive element and the second resistive element are measured. The controller 420 can determine the rate of air flow in the air duct based on the outputs of the first resistive element and the second resistive element. The difference between the detected resistances of the resistive elements can correspond to a change in flexure of the substrate. The change in flexure of the substrate can correspond to a predetermined air flow. When the detected air flow falls below a predetermined air flow threshold, the controller 520 can deactivate a subsystem of the oven, such as the heating element, to prevent overheating.

FIG. 11 illustrates a flow chart of exemplary method (600) according to an exemplary embodiment of the present disclosure. The method (600) can be implemented with any suitable appliance having a flexure sensing device, such as the flexure sensing devices illustrated in FIGS. 1-8. In addition, although FIG. 11 depicts steps performed in a particular order for purposes of illustration and discussion, the methods discussed herein are not limited to any particular order or arrangement. One skilled in the art, using the disclosures provided herein, will appreciate that various steps of the methods can be omitted, rearranged, combined and/or adapted in various ways.

At (610) an output of a first electrically resistive element can be detected and at (620) an output of a second electrically resistive element can be detected. The difference between the first electrically resistive element and the second electrically resistive element can be determined at (620). The difference between the outputs can be used to determine a change in the flexure of the sensor at (630). For instance, the difference between the outputs can be compared to a predetermined threshold and when the difference exceeds the threshold, a look-up table, algorithm, equation, and/or model can be used to determine a magnitude of the change in sensor flexure at (640). Based on the magnitude of the change in flexure, a subsystem of the appliance can be controlled at (650). In an alternative embodiment, the subsystem can be controlled based solely on the difference between the outputs without having to determine the magnitude of the change in flexure.

Figure 14:
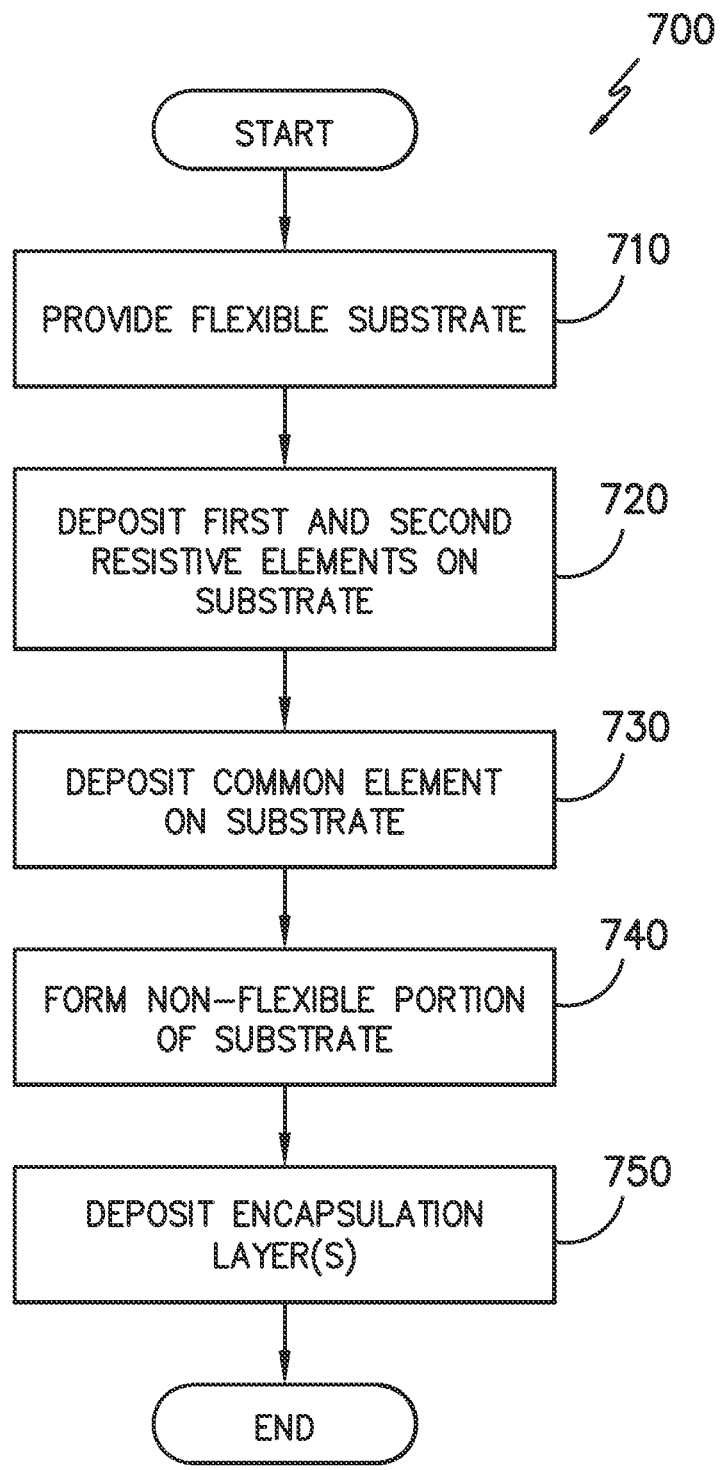
FIG. 14 depicts a flow diagram of an exemplary method of manufacturing a flexure sensor device according to an exemplary embodiment of the present disclosure.

FIG. 14 illustrates a flow chart of exemplary method (700) of manufacturing a flexure sensor according to an exemplary embodiment of the present disclosure. At (710), a flexible substrate can be provided. The flexible portion of the substrate can include any electrically insulating material that is suitable as a substrate and configured to retain form and shape while also being elastically flexible or bendable. For instance, the flexible material can be a resin, polymer, silicone, etc.

At (720), the method can include depositing the first and second resistive elements on the flexible substrate. For instance, the resistive elements deposited on the substrate using a silk-screen printing process such that the electrically resistive elements and are formed simultaneously. As shown at (730), a common element coupling the first and second electrically resistive elements can also be formed on the flexible substrate. The common element can be formed simultaneously with or separate from the first and second electrically resistive elements.

At (740), the method includes forming a non-flexible portion of the substrate such that the second resistive element is disposed within the non-flexible portion of the substrate. The non-flexible portion can be formed from a substantially rigid material that prevents flexing. For instance, the non-flexible portion can be a rigid material such as plastic, epoxy, bakelite, etc.

In one particular implementation, the non-flexible portion can be formed separately from the substrate and then applied to the flexible portion of the substrate. For instance, the non-flexible portion 120 can be injection molded and then coupled to the flexible portion of the substrate. Alternatively, the non-flexible portion of the substrate can be formed by modifying a portion of the flexible substrate. When the non-flexible portion of the substrate is formed separately, it can be coupled to the flexible portion such that it surrounds a portion of the flexible substrate. Alternatively, the non-flexible portion can be coupled to a top surface of the substrate and/or a bottom surface of the substrate.

Finally, the method can include depositing encapsulation layers on the substrate (750). The encapsulation layers can cover one or more portions of the substrate, such as the flexible portion and/or the non-flexible portion. The encapsulation layers can prevent the resistive elements from premature erosion. In addition, the encapsulation layers can prevent unwanted moisture from permeating the sensor. The material used for the encapsulation layers can be flexible so as to not impede the flexure of the flexible portion of the sensor.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they include structural elements that do not differ from the literal language of the claims, or if they include equivalent structural elements with insubstantial differences from the literal languages of the claims.

What is claimed is:

1. A method of manufacturing a flexure sensing device comprising:
    depositing first and second electrically resistive elements on or within a flexible substrate, the first electrically resistive element having a variable electrical resistance dependent on a change in flexure of the flexible substrate
    after depositing the first and the second electrically resistive elements on or within the flexible substrate, modifying the flexible substrate thereby forming a flexible portion and a non-flexible portion of the substrate, the flexible substrate being modified such that the second electrically resistive element is disposed on or within the non-flexible portion of the substrate and the first electrically resistive element is disposed on or within the flexible portion of the substrate;
    wherein the second electrically resistive element provides a reference resistance for the flexure sensing device and exhibits little or no change in resistance as the flexure sensor is flexed.

2. The method as in claim 1, wherein forming the non-flexible portion of the substrate comprises forming the non-flexible portion such that the second electrically resistive element is disposed exclusively on or within the non-flexible portion of the substrate.

3. The method as in claim 1, wherein depositing the first and the second electrically resistive elements comprises depositing the first electrically resistive element and the second electrically resistive element essentially simultaneously using the same material composition.

4. The method as in claim 1, further comprising depositing a common electrically conductive material on or within the substrate, the common conductive material coupled between the first electrically resistive element and the second electrically resistive element.

5. The method as in claim 4, wherein depositing the common electrically conductive material comprises depositing the common electrically conductive material that has a non-variable electrical resistance.

6. The method as in claim 1, wherein forming the non-flexible portion of the substrate comprises separately forming the non-flexible portion and then attaching the non-flexible portion to the flexible substrate.

7. The method as in claim 1, wherein forming the non-flexible portion of the substrate comprises forming the non-flexible portion on the flexible substrate.

8. The method as in claim 1, wherein forming the non-flexible portion of the substrate comprises forming the non-flexible portion to surround a portion of the flexible substrate.

9. The method as in claim 1, wherein forming the non-flexible portion of the substrate comprises forming the non-flexible portion of the substrate on a surface of the flexible substrate.

10. The method as in claim 1, wherein depositing the first and the second electrically resistive elements comprises depositing the first and the second electrically resistive elements using a same technique and a same material composition.

11. The method as in claim 1, wherein depositing the first and the second electrically resistive elements comprises depositing the first electrically resistive element on a first surface of the flexible substrate and depositing the second electrically resistive element on a second surface of the flexible substrate that is opposite to the first surface.

12. The method as in claim 1, further comprising depositing one or more encapsulation layers to cover at least a portion of one or more of the flexible substrate and the non-flexible portion.

13. The method as in claim 1, wherein depositing the first and the second electrically resistive elements comprises performing a silk-screen printing process to deposit the first and the second electrically resistive elements on the flexible substrate.

14. The method as in claim 1, wherein depositing the first and the second electrically resistive elements comprises performing a metal sputtering technique to deposit the first and the second electrically resistive elements on the flexible substrate.

15. The method as in claim 1, wherein depositing the first and the second electrically resistive elements comprises depositing the first and the second electrically resistive elements such that each of the first and the second electrically resistive elements has a rectangular U-shape.

16. The method as in claim 1, wherein depositing the first and the second electrically resistive elements comprises depositing the first and the second electrically resistive elements such that each of the first and the second electrically resistive elements has a non-linear symmetrical shape.

17. The method as in claim 1, wherein depositing the first and the second electrically resistive elements comprises depositing the first and the second electrically resistive elements such that the first and the second electrically resistive elements have a same width as each other.

18. The method as in claim 17, wherein depositing the first and the second electrically resistive elements comprises depositing the first and the second electrically resistive elements such that the first electrically resistive element has a first length and the second electrically resistive element has a second length that is less than the first length.

19. The method as in claim 1, further comprising mounting the flexure sensing device directly to a printed circuit board.

* * * * *